United States Patent [19]

Homsy

[11] Patent Number: 5,002,488

[45] Date of Patent: Mar. 26, 1991

[54] DENTAL IMPLANTS WITH RESORPTION PREVENTING MEANS

[75] Inventor: Charles A. Homsy, Houston, Tex.

[73] Assignee: Hadaco, Ltd., Tortola, British Virgin Isls.

[21] Appl. No.: 180,466

[22] Filed: Apr. 12, 1988

[51] Int. Cl.⁵ .............................................. A61C 13/28
[52] U.S. Cl. ..................................... 433/169; 433/173
[58] Field of Search ............... 433/169, 173, 174, 175, 433/176

[56] References Cited

U.S. PATENT DOCUMENTS

| | | | |
|---|---|---|---|
| 3,808,606 | 5/1974 | Tronzo | 433/173 |
| 3,863,344 | 2/1975 | Pillet | 433/173 |
| 4,011,602 | 3/1977 | Rybicki et al. | 433/173 |
| 4,051,598 | 10/1977 | Sneer | 433/175 |
| 4,252,525 | 2/1981 | Child | 433/173 |
| 4,424,037 | 1/1984 | Ogino et al. | 433/173 |
| 4,531,916 | 7/1985 | Scantlebury et al. | 433/173 |
| 4,568,285 | 2/1986 | Chiaramonte et al. | 433/169 |
| 4,731,085 | 3/1988 | Koch | 433/173 |
| 4,772,203 | 9/1988 | Scheunemann | 433/173 |
| 4,812,120 | 3/1989 | Flanagan et al. | 433/173 |

Primary Examiner—Gene Mancene
Assistant Examiner—Adriene B. Lepiane
Attorney, Agent, or Firm—Michael P. Breston

[57] ABSTRACT

The dental prosthesis is adapted for insertion into a socket formed within the patient's jaw. It comprises an elongated shaft defining a proximal region, a distal region, and a tip. A soft porous pad extends distally from the shaft tip. The distal region is preferably biocompatible, porous, soft, resilient, deformable, tissue-ingrowth promoting, and has a compressive stress per unit of strain which is substantially smaller than that of adjacent bone.

37 Claims, 1 Drawing Sheet

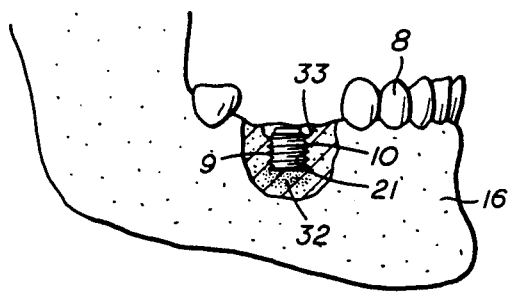
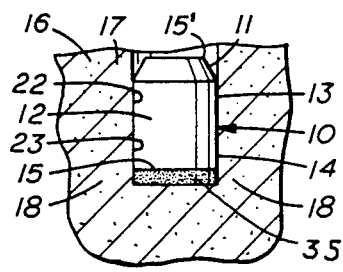
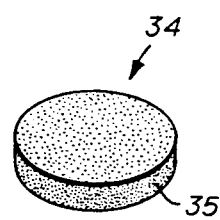
FIG. 1 (PRIOR ART)    FIG. 2    FIG. 3
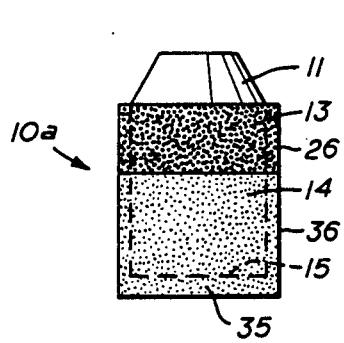
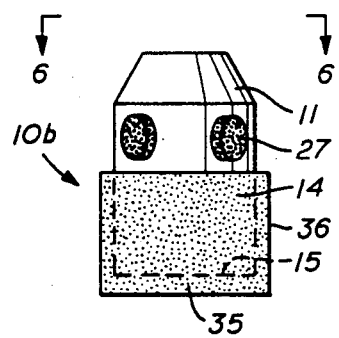
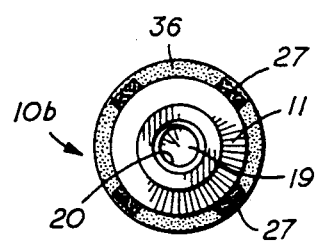
FIG. 4    FIG. 5    FIG. 6
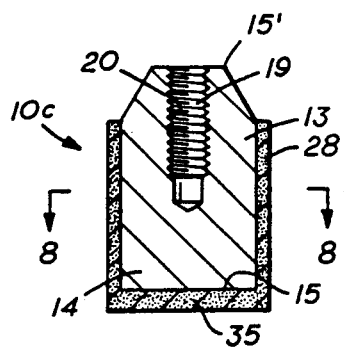
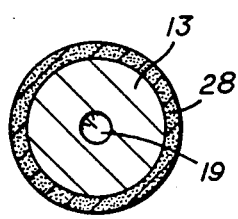
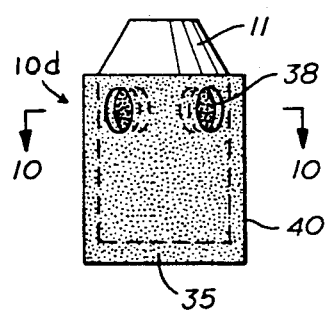
FIG. 7    FIG. 8    FIG. 9
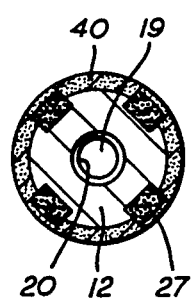
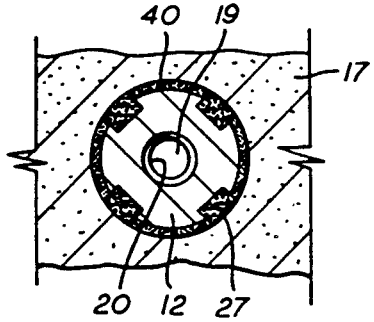
FIG. 10    FIG. 11

DENTAL IMPLANTS WITH RESORPTION PREVENTING MEANS

This application is related to application of Ser. No. 07/07/180,467, filed on even date.

BACKGROUND OF THE INVENTION

1. Field of the Invention

The invention relates to dental implants of the type which include a shaft for insertion into the mandible and/or maxilla.

2. Description of the Prior Art

The dental implant is typically made out of titanium. It is inserted into a precisely drilled socket. New bone will grow up and then interface and adapt to the titanium shaft.

The latest dental implants have shafts which receive a hydroxylapatite coating that permits bone to actually bond thereto. The shafts are generally cylindrical in shape and have various lengths typically from 7 mm to 18 mm to accommodate individual anatomy.

The shaft receives a particular fixed or removable abutment attachment to meet the anatomical limitation requirements of individual patients.

All removable abutments are interchangeable in the shaft. The abutments have inserts with cemented or threaded connections.

Threaded inserts allow for a change of restoration type without disrupting the integrity of the dental implant itself.

Each insert may accept a viscoelastic intramobile element which is intended to absorb and distribute stress, and which imitates the function of the tooth, periodontal ligament, and alveolar bone.

Thus, the restorative dentist or oral surgeon can select from different dental implants systems as alternatives to fixed or removable prosthetics for use in the edentulous or partially edentulous mandible and maxilla. He can choose from endosseous implants which become biointegrated or osseointegrated. These dental implants include those which rely on an accurate press-fit to become established between an uncoated shaft and the surrounding bone, and those which rely on tissue ingrowth into a porous coating on the outer shaft surface. A postoperative mechanical bond is formed between living bone and the coated surface. This bond is known as biointegration.

The coating can also be designed to form a postoperative mechanical biochemical bond with the living bone. This bond is known as osseointegration.

Unfortunately, clinical evidence has shown that the various attempts, at using hard porosities for achieving long-lasting, adequate load transfer and implant stability and fixation, have not been entirely satisfactory because the jaw bone under the shaft tip will increasingly shunt the load from the proximal bone to the distal bone in the region apposite to the shaft tip, and will lead to proximal bone resorption, which tends to reduce the proximal bone's resistance to implant swaying. This tendency further accelerates the bone resorption process, which is unavoidably accompanied by implant instability, great discomfort, and severe pain.

It is an object of this invention to provide different types of dental implants, each having bone resorption preventing means that alleviate the load shunting problem and the resulting proximal bone resorption.

SUMMARY OF THE INVENTION

The relatively intense axial and swaying cyclic strain and stresses which would be transmitted by the distal tip of the shaft to the apposite bone are relieved in accordance with this invention by an extension which is added to the tip of the distal shaft. This extension substantially eliminates or attenuates the transfer of these stresses by the distal shaft to the apposite bone.

Each dental implant is adapted for insertion into a preformed socket within the mandible or maxilla. Each comprises a shaft defining a proximal surface, a distal surface, and a tip. A soft porous pad extends distally from the shaft tip. The distal surface is preferably biocompatible, porous, soft, resilient, deformable, and tissue-ingrowth promoting.

In another embodiment, the shaft surface is substantially entirely biocompatible, porous, soft, resilient, deformable, and tissue-ingrowth promoting.

In a further embodiment, at least a portion of the proximal surface is biocompatible, porous, deformable, and tissue-ingrowth promoting, and another portion of the proximal surface is biocompatible, porous, nondeformable, and tissue-ingrowth promoting.

BRIEF DESCRIPTION OF THE DRAWINGS

FIG. 1 is an elevational view, partly in section, of a known uncoated dental prosthesis with a corrugated or threaded surface screwed into a threaded socket in the jaw, in which the bone under the shaft tip is nearly totally densified, and in which the bone resorption process has already well progressed;

FIG. 2 is an elevational view of an uncoated dental prosthesis together with a simple embodiment of the invention, which includes a soft, porous, biocompatible pad;

FIG. 3 is a perspective view of the pad shown in FIG. 2;

FIG. 4 is an elevational view of a dental prosthesis whose shaft is coated with porous metal on its proximal surface, and which includes the pad of FIG. 3 and also a soft, porous, biocompatible distal sleeve or coating extending upwardly from the pad on the bare surface of the shaft;

FIG. 5 is an elevational view of a dental prosthesis coated with discrete porous metal patches on the surface of its proximal shaft and which utilizes the pad shown in FIG. 3 and the sleeve shown in FIG. 4.

FIG. 6 is a top view on line 6—6 of FIG. 5;

FIG. 7 is an elevational sectional view of a dental prosthesis whose shaft is fully coated with a very soft porous layer, and which utilizes the pad below its shaft tip;

FIG. 8 is a sectional view on line 8—8 of FIG. 7;

FIG. 9 is an elevational view of a dental prosthesis coated with discrete porous metal patches on the surface of its proximal shaft; it also has a soft, porous, biocompatible sleeve or coating over the entire bare surface of the shaft, and utilizes the pad of FIG. 3 below the shaft tip;

FIG. 10 is a sectional view on line 10—10 of FIG. 9; and

FIG. 11 is a sectional view similar to FIG. 10, but showing the porous soft coating as being compressed by the wall of the socket.

DETAILED DESCRIPTION OF PREFERRED EMBODIMENTS

The same numerals will be used to designate the same or similar parts, whenever possible, to emphasize the novel aspects of the invention.

A brief description of a prior art dental prosthesis 10 (FIG. 1) within a preformed socket within the mandible will facilitate the understanding of the problems solved by the invention.

The dental implants include a shaft for insertion into the mandible and/or maxilla. Only the mandible will be described hereinafter to simplify the description.

The shafts are generally cylindrical in shape and have various lengths typically from 7 mm to 18 mm to accommodate individual anatomy.

Each shaft receives a particular fixed or removable abutment attachment (not shown) to meet the anatomical limitation requirements of individual patients. All removable abutments are interchangeable in the shaft. The abutments have inserts which are cemented or threaded into the shaft's axial bore 19 on threads 20 (FIGS. 6-8 and 10-11).

Threaded inserts allow for a change of restoration type without disrupting the integrity of the dental implant itself.

Each insert may accept a viscoelastic intramobile element (not shown) which is intended to absorb and distribute stress, and which imitates the function of the missing tooth 8 (FIG. 1), periodontal ligament, and alveolar bone.

This invention provides different types of dental implants, each having bone resorption preventing means that alleviate the load shunting problem and the resulting proximal bone resorption.

Implant 10 (FIGS. 1-2) includes a neck 11 and a stem 12 which has a proximal exterior or outside region 13, a distal exterior or outside region 14, and a distal tip 15. Neck 11 has a top annular edge 15'. As used herein in respect to stem 12, the word "region" may be a three-dimensional locus of points which has depth. For example, distal stem region 14 can be a layer, or a coating, or the exterior surface of stem 12 which can be smooth (FIG. 2) or it may have threads or corrugations 9 (FIG. 1).

If accurately fitted, stem 12 can transfer appropriate stresses to the jaw bone 16, which has a proximal region 17 and a distal region 18. The surgeon drills within the jaw a cylindrical socket 21, which has a proximal region 22 and a distal region 23. In an attempt to avoid intruding into viable bone, stem 12 is shaped to seat centrally in socket 21.

When the exterior surface of shaft 12 is threaded or corrugated then socket 21 is tapped to accommodate in intimate contact the corrugations or threads 9.

For use with the uncoated implant 10, the surgeon uses precision tools for drilling, and in threaded implants for tapping, a generally cylindrical socket 21 to conform as closely as possible to the geometrical shape of its stem 12. It is intended to obtain, intraoperatively, a generally uniform press fit between stem 12 and the appositional jaw bone 16.

If a perfect press-fit is achieved, the prepared socket 21 has, at each point over substantially its entire length, a transverse sectional area which corresponds substantially with the corresponding transverse sectional area of stem 12 at that point.

An implant 10 which combines a uniform press-fit between proximal stem 13 and the appositional bone 16 can transfer loads to proximal bone 17 so as to develop strains therein that are similar to those imposed on normal teeth 8 within an intact jaw bone 16.

In response to loads, proximal stem 13 distributes stresses longitudinally in the form of compressive stresses to tip 15 and in the form of lateral stresses to proximal bone 17. Distal stem 14 and/or its stem tip 15 transfer corresponding stresses and strains to the apposite distal bone 18. Distal bone 18 may respond to the received stresses by densifying its bone structure, and especially under stem tip 15.

Such densified bone 32 (FIG. 1) is believed to be prompted by relatively intense stresses which are transmitted, at least in part, through stem tip 15 to the apposite bone. Such stresses are believed to be caused by axial forces acting about the long axis of stem 12 in response to normal jaw movements.

Densified bone 32 has the necessary strength to fully react against the physiological mastication loads transmitted to and/or through stem tip 15.

The more reaction forces that are provided by more or less densified bone 32, the less reaction forces will be needed from proximal bone 17. This principle is known as "load shunting" from proximal bone 17 to distal bone 18.

It is believed that the transfer by distal shaft 14, and/or its shaft tip 15, of stresses and strains to the apposite bone 18, and the consequential formation of more or less densified bone 32, are the primary causes for the proximal, gradual, osseous resorption, generally designated as 33 (FIG. 1), which takes place within proximal bone 17.

As the decalcification or osseous resorption 33 increases, proximal bone 17 becomes less and less able to resist the dangerous and increasing tendency of proximal shaft 13 to sway within proximal socket 22, as well as the tendency by shaft tip 15 to toggle. All of which further prompts bone 16 to stimulate osseous densification under shaft tip 15, which further accelerates the proximal osseous resorption 33 already in progress until, sooner or later, sufficient loosening of shaft 12 within its socket 21 takes place, which is accompanied by great pain and extraordinary discomfort to the patient.

In order to eliminate or substantially reduce the bone's resorption, there is provided, in accordance with this invention, an energy absorbing means 34 (FIGS. 2-3) which is designed to substantially absorb the mechanical energy that is being transferred to and/or through distal shaft 14 and/or its tip 15, or at least to largely attenuate the intensity of such loads that do transfer, to the apposite bone in the distal region 18 of bone 16.

The present invention has utility for uncoated dental prostheses and for those prostheses whose shafts receive hard surface porosities, as will now be illustrated.

Implant 10 (FIGS. 1-3) has an uncoated shaft 12 which is associated with a simple embodiment of the energy absorbing means 34. This embodiment is a pad 35 which is an extension of or is bonded to shaft tip 15 (FIGS. 2-5, 7, 9).

Implant 10a (FIG. 4) has a proximal shaft region 13 which is coated with a continuous thin, hard porous coating 26. In accordance with this invention, the energy absorbing means 34, in addition to pad 35, also includes a soft, porous, distal sleeve or coating 36 extending upwardly from and being continuous with pad 35. Coating 36 is applied to the bare metal of shaft 12 in a suitable manner to fix it securely thereto. Soft sleeve 36 is confined mainly to the distal shaft region 14.

Pad 35 and coating 36 serve to absorb or largely attenuate the longitudinal, lateral, and swaying stresses and micromotions transferred to distal shaft 14.

Such energy absorption or attenuation in the region appositional to distal shaft tip 15 prevents unnatural load shunting to distal bone 18 and, more importantly, reduces localized stress zones therein, thereby fostering favorable conditions for long-term fixation of proximal shaft 13, maintaining its load transfer capabilities, and ensuring the osseous integrity of proximal bone 17.

Implant 10b (FIG. 5-6) has a proximal shaft region 13, which is coated with discrete hard porous patches 27, and a distal shaft region 14, which receives pad 35 and sleeve 36.

It is intended that when proximal shaft 13 is inserted into proximal socket 22, a press-fit will form at least between the hard coatings and the apposite proximal bone 17. To allow for a press-fit of soft coating 36, socket 21 is made to have, at each point adjacent to the soft coating 36, a transverse sectional area which is slightly less than the corresponding transverse sectional area of soft coated stem 12 at that point.

At the junction between hard and soft coatings on the stem of implant 10a, the soft coated cross-sections will be larger than adjacent hard-coated cross-sections, so that following compression of the soft coating, the hard coating will have a press-fit against adjacent proximal bone 17.

Implant 10c (FIGS. 7-8) has a shaft 12 which is substantially fully coated with a very soft, tissue-ingrowth promoting, very porous coating 28 over its entire bare outer surface. The distal shaft region 14 of implant 10c receives pad 35 below shaft tip 15.

Implant 10d (FIGS. 9-10) has discrete, hard porous patches 38 on the proximal shaft region 13. The entire remainder of the bare outer surface of shaft 12 is coated with a soft, porous coating 40. Distal shaft region 14 also receives pad 35 below shaft tip 15.

To use implants 10c and 10d, the surgeon shapes socket 21 (FIG. 1-2) to conform as perfectly as possible to the geometric shape of shaft 12. To allow for the compression of soft coating 28 or soft coating 40, socket 21 is made to have, at each point over substantially its entire length, a transverse sectional area which is slightly less than the corresponding transverse sectional area of coated shaft 12 at that point.

The soft porous coating must compress by a sufficient amount so as to reduce the overall dimension of the coated shaft to that of the hard porous coatings 27 or 38 (compare FIGS. 10 and 11).

When coated shaft 12 is forcefully inserted into socket 21, each one of soft porous coatings 28, 36, or 40 becomes compressed (FIG. 11) and provides a desired press-fit, thereby achieving an optimal initial stability and an extensive surface contact area between the compressed porous coating and the appositional hard bone 16.

A compression of the soft coating by about 1 to 40% will bring the hard porous metal coating into apposition with adjacent bone to maximize the possibility of bone ingrowth into the porous metal. At the same time such biological bonding with the hard coating will be augmented by fibrous tissue an/or bone ingrowth into the soft deformed coating.

The compression is preferably such that the sectional shape of coated proximal shaft 13 at any given point is slightly larger than the corresponding dimension of socket 22 at that point, whereby, when shaft 12 is inserted into socket 21, soft porous coating 28 or 40 becomes compressed between the core of shaft 12 and the appositional bone, but without substantially restricting the porosity of the soft coating.

The opportunity for tissue ingrowth into the soft and hard coatings provides an optimal initial and a long-term stability, as well as a distributed rather than a multi-point biological fixation.

Implants 10 and 10a-10d are typically made of a strong, hard, biocompatible metal, such as stainless steel, cobalt-chrome, or titanium. They may also be made of a sufficiently strong composite biocompatible structure of metal with polymers, or of wholly polymeric structures, which may be reinforced with metal or ceramic or other materials, such as polyimide fiber or carbon fiber. If the implant is uncoated (FIG. 2), new bone will grow up and then interface and adapt to shaft 12.

The biocompatible hard, tissue-ingrowth promoting, surface porosities 26, 27 and 38 can be ceramic, polymeric, metallic or a composite material thereof. These surface porosities can be either wholly or partially of a homogeneous porous phase, or they can be combinations of different porous phases. They can be made of porous titanium or other biocompatible metal, and said metal porosities can in turn be coated with synthetic hydroxylapatite to allow for a strong bond to form with appositional proximal hard bone 17 (FIG. 11).

A postoperative mechanical bond is formed between the living and the hard porous coated surfaces. This bond is known as biointegration.

The hard porous coatings can also be designed to form a postoperative mechanical biochemical bond with the living bone. This bond is known as osseointegration.

Hard porous coatings can be on the surface of proximal shaft 13 (FIG. 6), or they can be countersunk into the shaft body (FIG. 10).

The material out of which pad 35 and soft coatings 28, 36 and 40 are made should preferably have a three-dimensional structure characterized by at least a low-modulus of elasticity, a continuous biocompatible solid phase, and a biocompatible fluid phase. Obviously, before pad 35 is implanted into the bone, the fluid phase is air in the ambient environment.

In the preferred embodiment, the fluid phase is continuous with the ambient environment. This preferential structure should exhibit a compressive stress-strain behavior of a substantially lower order than or bone. That is, it must deform under load much more readily than the appositional bone.

The material for pad 35 and the soft coatings can have an open pore size of 50 to 400 micro-millimeters which has been found to be optimal. A material that meets the above criteria can be elastomeric or nonelastomeric, resilient, open or closed pore, and very soft, so that sufficient deformation in its shape can occur in response to loading by distal shaft 14, as well as by any subsidence of shaft 12.

This soft porous material for pad 35 should become compressed in response to an initial loading, but without substantially restricting its porosity, thereby permitting a subsequent compression to take place. Such a material will be nonstimulating to the distal bone region 18.

The porosity of pad 35 will allow the ingrowth therein of fibrous tissue, which will further enhance its ability to attenuate or absorb energy transferred to distal shaft 14.

Pad 35 has a porosity such that its volume can shrink up to 60–80% of its original volume before substantial resistance to compression becomes manifest.

Pad 35 (FIG. 2) can be a short cylinder having an outer diameter which is slightly less than the smallest diameter of socket 21 to facilitate the insertion of shaft 12 therein, or it can be slightly larger than the diameter of distal socket 23 to obtain a pressure fit with the appositional hard bone 18.

It has been found that the thickness for the material from which pad 35 is made, between its interior surface apposite to the shaft tip 15 and its outside surface, should be greater than 0.5 mm and preferably greater than 2 mm and less than 4 mm to provide adequate bio-mechanical energy absorption.

The porous distal shaft region preferably has a thickness less than 2.5 mm. The thickness of the soft, resilient and deformable soft coatings may be such that the overall dimensions of the coated shaft exceed the corresponding dimensions of the prepared socket 21 by an amount ranging from 0.2% to 10%.

It has been found that the thickness for the material from which the soft coatings are made should be greater than 0.5 mm and preferably less than 2.5 mm.

The diametrical dimension where the hard coatings are located correspond to that of the opposite proximal socket.

The thickness of the soft coatings is such that they may be compressed by an amount ranging from one percent (1%) to forty percent (40%) of their original thickness without having their porosities overly reduced.

The material out of which pad 35 and soft coatings 28, 36 and 40 are made can be a porous Teflon perfluorocarbon polymer. Such materials including tissue-ingrowth promoting additives are sold by Vitek, Inc., under the trademark PROPLAST.

A PROPLAST material is a reinforced polymer which comprises polytetrafluoroethylene fibers, in admixture with a proportion of carbon or graphite fiber or particles, or aluminum oxide particles and bonded with a sintered polytetrafluoroethylene resin.

The PROPLAST materials are soft, very porous, open pore, ingrowth-promoting, compressible, and permanently deformable under very light loads.

This invention fills the need for more natural stress and strain patterns within bone 16 by optimizing the conditions for intimate engagement by shaft 12 with appositional bone 16.

The present invention allows for a more stable apposition of porous metal to adjacent bone, thereby achieving an improved distributed longitudinal load transfer to bone 16. The forces per unit of surface area become largely reduced.

By imposing at a suitable time postoperatively a cyclical load on proximal bone 17 analogous to the load of a natural, unoperated mandible, proximal bone 17 responds and maintains maximal strength and resistance to shaft swaying.

Thus, the surgeon can select from different dental prostheses including those which rely on an accurate press-fit to become established between an uncoated shaft and the surrounding bone, and those which rely on tissue ingrowth into a porous coating on the outer shaft surface.

He can choose from implants which are threaded, uncoated, coated with a very soft porous material, or coated with a hard porous material, or with a combination thereof.

WHAT I CLAIM IS:

1. A dental prosthesis for insertion into a socket formed within a patient's jaw, comprising:
    (1) an elongated stem having an outer region including:
        (a) a proximal region, and
        (b) a distal region having a distal tip,
    (2) said distal tip having an energy-absorbing member, and
    (3) said member
        (a) having a thickness measured in the axial direction of said stem,
        (b) being biocompatible, resilient, porous and soft, and
        (c) having a compressive stress per unit of strain which is substantially smaller than that of adjacent bone.

2. A dental prosthesis according to claim 1, in which said energy-absorbing member is tissue-ingrowth promoting, and said thickness of said member in said axial direction is greater than 0.5 mm and less than 4 mm.

3. A dental prosthesis according to claim 1, in which said energy-absorbing member sustains, in use, a substantial deformation in its original shape in response to loading by said stem without substantially restricting its porosity.

4. A dental prosthesis according to claim 3, in which said member's volume can shrink up to 60–80% of its original volume in response to said loading by said stem.

5. A dental prosthesis according to claim 1, in which said energy-absorbing member has a three-dimensional structure having a low-modulus of elasticity compared to that of said bone, and said structure having a continuous biocompatible solid phase and a biocompatible fluid phase.

6. A dental prosthesis according to claim 5, in which said energy-absorbing member is elastomeric, and said member sustains, in use, a substantial permanent deformation in its original shape in response to loading by said stem without substantially restricting its porosity.

7. A dental prosthesis according to claim 6, in which said energy-absorbing member is permanently deformable under very light loads.

8. A dental prosthesis according to claim 6, in which said member's volume can shrink up to 60–80% of its original volume in response to said loading by said stem.

9. A dental prosthesis according to claim 5, in which said biocompatible fluid phase is continuous with the fluid in the ambient environment surrounding said dental prosthesis.

10. A dental prosthesis according to claim 9, in which said biocompatible fluid phase is air when said prosthesis is initially inserted into said socket within said patient's jaw.

11. A dental prosthesis according to claim 9, in which said energy-absorbing member is non-elastomeric.

12. A dental prosthesis according to claim 11, in which said biocompatible solid phase of said energy-absorbing member defining pores having an average effective diameter of 50 to 400 microns.

13. A dental prosthesis according to claim 9, in which said biocompatible solid phase of said energy-absorbing member defining pores having an average effective diameter of 50 to 400 microns.

14. A dental prosthesis according to claim 5, in which said biocompatible solid phase of said energy-absorbing member comprises polytetrafluoroethylene fibers, in admixture with carbon fiber and bonded with a sintered polytetrafluoroethylene resin.

15. A dental prosthesis according to claim 5, in which said biocompatible solid phase of said energy-absorbing member comprises polytetrafluoroethylene fibers, in admixture with graphite fiber and bonded with a sintered polytetrafluoroethylene resin.

16. A dental prosthesis according to claim 5, in which said biocompatible solid phase of said energy-absorbing member comprises polytetrafluoroethylene fibers, in admixture with aluminum oxide particles, and bonded with a sintered polytetrafluoroethylene resin.

17. A dental prosthesis according to claim 5, in which said solid phase of said energy-absorbing member is a reinforced polymer.

18. A dental prosthesis according to claim 1, in which at least a portion of said distal region of said stem having integral therewith biocompatible, resilient, porous and soft means which promotes tissue-ingrowth therein.

19. A dental prosthesis according to claim 18, in which said porous soft means having a thickness less than 2.5 mm.

20. A dental prosthesis according to claim 19, in which said porous soft means having a resiliency such that it can be compressed by an amount ranging from one percent (1%) to forty percent (40%) of its original thickness.

21. A dental prosthesis according to claim 20, in which said porous soft means defining pores having an average effective diameter of 50 to 400 microns.

22. A dental prosthesis according to claim 1, in which substantially the whole of said proximal and distal regions of said stem having integral therewith biocompatible, resilient, porous and soft means which promotes tissue-ingrowth therein.

23. A dental prosthesis according to claim 22, in which said porous soft means having a thickness less than 2.5 mm.

24. A dental prosthesis according to claim 23, in which said porous soft means having a resiliency such that it can be compressed by an amount ranging from one percent (1%) to forty percent (40%) of its original thickness.

25. A dental prosthesis according to claim 24, in which said porous soft means defining pores having an average effective diameter of 50 to 400 microns.

26. A dental prosthesis for insertion into a socket formed within a patient's jaw, comprising: an elongated stem having an outer region including: a proximal region, a distal region, and a distal tip; said distal tip having an energy-absorbing, biocompatible, resilient, soft, porous member having a thickness, measured in the axial direction of said stem, and having a compressive stress per unit of strain which is substantially smaller than that of apposite bone within said socket; and at least a potion of said proximal region of said stem having integral therewith a biocompatible, porous and hard means which promotes tissue-ingrowth, and said hard means having a modulus of elasticity at least as great as that of said bone.

27. A dental prosthesis according to claim 26, and another portion of said proximal region of said stem having integral therewith biocompatible, porous and soft means which promotes tissue-ingrowth therein.

28. A dental prosthesis according to claim 27, in which at least a portion of said distal region of said stem having integral therewith biocompatible, resilient, porous and soft means which promotes tissue-ingrowth therein.

29. A dental prosthesis according to claim 28, in which said porous soft means having a thickness less than 2.5 mm.

30. A dental prosthesis according to claim 29, in which said porous shaft means having a resiliency such that it can be compressed by an amount ranging from one percent (1%) to forty percent (40%) of its original thickness.

31. A dental prosthesis according to claim 30, in which said porous soft means defining pores having an average effective diameter of 50 to 400 microns.

32. A dental prosthesis according to claim 27, in which at the junction between said porous hard means and said porous soft means, the cross-section of said soft means is larger than that of said hard means so that, upon insertion of said stem into said socket and following compression of said soft means, said hard means have a press-fit against apposite bone in said socket.

33. A dental prosthesis according to claim 26, in which apart from said hard means, substantially the whole of the remainder of said outer region of said stem having integral therewith biocompatible, resilient, porous and soft means which promotes tissue-ingrowth therein.

34. A dental prosthesis according to claim 33, in which said porous soft means having a thickness less than 2.5 mm.

35. A dental prosthesis according to claim 34, in which said porous soft means having a resiliency such that it can be compressed by an amount ranging from one percent (1%) to forty percent (40%) of its original thickness.

36. A dental prosthesis according to claim 35, in which said porous soft means defining pores having an average effective diameter of 50 to 400 microns.

37. A dental prosthesis according to claim 26, in which said energy-absorbing member is tissue-ingrowth promoting, and said thickness of said member in said axial direction is greater than 0.5 mm and less than 4 mm.

* * * * *